United States Patent [19]

Walfield et al.

[11] Patent Number: 4,978,623

[45] Date of Patent: Dec. 18, 1990

[54] METHODS AND COMPOSITIONS FOR EXPRESSION OF BTI ENDOTOXIN

[75] Inventors: Alan M. Walfield; Thomas J. Pollock, both of San Diego, Calif.

[73] Assignee: Snytro Corporation, Lenexa, Kans.

[21] Appl. No.: 8,069

[22] Filed: Jan. 13, 1987

Related U.S. Application Data

[63] Continuation of Ser. No. 582,506, Feb. 22, 1984, abandoned.

[51] Int. Cl.$^5$ ............... C12N 1/21; C12N 15/32; C12N 15/63; C12N 15/70
[52] U.S. Cl. ............... 435/320; 435/69.1; 435/71.1; 435/91; 435/170; 435/172.1; 435/172.3; 435/252.3; 435/252.33; 435/832; 435/848; 536/27; 935/6; 935/9; 935/22; 935/23; 935/29; 935/59; 935/60; 935/64; 935/72; 935/73; 935/74
[58] Field of Search ............... 435/68, 91, 170, 172.1, 435/172.3, 253, 832, 848, 69.1, 71.1, 252.3, 252.33, 320; 935/6, 9, 22, 23, 29, 59, 60, 64, 72, 73, 74; 536/27

[56] References Cited

U.S. PATENT DOCUMENTS 4,467,036  8/1984  Schnepf et al. ............... 435/317
4,652,628  3/1987  Walfield et al. ............... 530/324

OTHER PUBLICATIONS

Ward et al. 1984, "Cloning and Expression in E. coli of the Insecticidal δendotoxin gene . . . ", FEBS v175(2) pp. 377–382.
Fitz-James 1982 "Symposium on B. thuringiensis var israelensis H-14: A bacterial insecticide", 7th Ann. Ontario Mosquito Control Association Meeting, Mar. 1–2, 1982.
Schnepf et al., 1981, "Cloning and Expression of the Bacillus thuringiensis crystal protein gene in E. coli", Proc. Natl. Acad. Sci. vol. 78, pp. 2893–2897.
Sekar et al., 1985, "Molecular Cloning of the delta-endotoxin gene of Bacillus thuringiensis var israelensis", Gene , vol. 33 pp. 151–158.
Gonzalez Jr., 1982, "Transfer of B. thuringiensis plasmids coding for δ-endotoxin . . . ", Proc. Natl. Acad. Sci., vol. 79 pp. 6951–6955.
Ward et al., 1983, "Assignment of the δ-endotoxin gene of Bacillus thuringiensis var israelensis to a specific plasmid . . . ", FEBS vol. 158 pp. 45–49.
Thorne et al. 1986, J. Bacteriol. 166(3):801–811.
Bourgouin et al. 1986 MGG 205:390–397.
Garduro et al., 1988, App. Environ. Microbiol. 54(1):277–279.
Ward et al., "Bacillus thuringiensis var. israelensis δ-Endotoxin", in J. Mol. Biol. (1986) 191:1–11.
Waalwijk, et al., "Molecular cloning and the nucleotide sequence of the M$_r$ crystal protein gene of Bacillus thuringiensis subsp. israelensis", in Nucleic Acids Research (1985) 13:8207–8217.

Primary Examiner—Richard A. Schwartz
Assistant Examiner—Richard C. Peet
Attorney, Agent, or Firm—Bertram I. Rowland

[57] ABSTRACT

DNA sequences are provided coding for Bacillus thuringiensis var. israelensis (BTI) endotoxin, employing bacterial hosts which produce a protein having insecticidal activity for dipteran insects.

The bacteriophage lambda strain SYN A4-1 was deposited at the A.T.C.C. on Feb. 22, 1984, and given Accession No. 40098.

4 Claims, No Drawings

METHODS AND COMPOSITIONS FOR EXPRESSION OF BTI ENDOTOXIN

This is a continuation of Ser. No. 582,506, filed Feb. 22, 1984, now abandoned.

BACKGROUND OF THE INVENTION

Field of the Invention

The ability to isolate DNA sequences coding for naturally-occurring polypeptides and introducing the isolated sequences into foreign hosts for expression of the encoded polypeptide has greatly expanded the opportunities to produce polypeptides or analogs thereof having biological activity. As more is learned about the mechanism of expression in both prokaryotes and eukaryotes, there is an expanding appreciation of the sophistication of the mechanisms of transcription and translation, as well as replication, and the interaction of naturally-occurring segments, both coding and non-coding. While various techniques have been developed which aid in the isolation, sequencing and synthesizing of DNA and peptides, each investigation of expression of a new polypeptide frequently results in unanticipated obstacles, which require new approaches or modifications of existing techniques.

It has long been known that *B. thuringiensis* species produce a variety of proteins having insecticidal activity. Because of their natural nature, biodegradability, and the apparent absence of insect resistance to their toxicity, these insecticides have attracted much interest. However, due to the difficulties of growing the host for producing the insecticidal protein, the use of these naturally-occurring insecticides has been somewhat limited. It has therefore become of interest to develop DNA sequences coding for proteins having the same or analogous properties to the naturally-occurring *B. thuringiensis* insecticides.

Description of the Prior Art

The *Bacillus thuringiensis* var. *israelensis* (BTI) endotoxin has been suggested to be associated with the large plasmids of this species. Kamdar and Joyaraman, *Biochem. Biophys. Res. Commun.* (1983) 110:477–482; and Clarke et al., (1983) *Abstracts of the Annual Meeting of the American Society for Microbiology:* H91. Properties of BTI endotoxin are described by Thomas and Ellar, *J. Cell Sci.* (1983) 60:181–197; Tyrell et al., J. Bacteriol. (1981) 145:1052–1062; and Clarke et al., supra. Properties of the kurstaki endotoxin as produced by recombinant plasmids is described in Schnepf and Whitely, *Proc. Natl. Acad. Sci. USA* (1981) 78:2893–2897, reporting that a soluble, rather than crystalline form is obtained.

SUMMARY OF THE INVENTION

Methods are provided for isolating a DNA sequence coding for a polypeptide having an apparent molecular weight of 58,000 daltons on polyacrylamide-SDS gels and having toxicity to *dipteran* insects. Particularly, a strain of *B. thuringiensis* var. *israelensis* is employed as a source of plasmid DNA and the plasmid DNA isolated from which a DNA sequence containing the gene encoding for an insecticidal polypeptide is excised. The DNA sequence is introduced into an appropriate extrachromosomal vector for introduction into a compatible bacterial host for production of an insecticidal polypeptide having a biological property analogous to the BTI endotoxin.

DESCRIPTION OF THE SPECIFIC EMBODIMENTS

Novel DNA sequences and constructions are provided for use in methods for expressing insecticidal polypeptides. The insecticidal polypeptides are found to have a biological property(ies) analogous to the endotoxin of *Bacillus thuringiensis* var. *israelensis (BTI)*.

In accordance with the method, a strain of BTI is employed as a source for a DNA sequence coding for an insecticidal polypeptide having an apparent molecular weight of 58,000 daltons on polyacrylamide-SDS gels. To enhance the available amount of DNA, the organism is grown at 32° C. in modified SP4 medium to log phase, lysed and plasmid DNA isolated (Kronstad et al., *J. Bacteriol.* (1983) 154:419–428).

The plasmid DNA is then treated in manner to concentrate DNA fragments isolated from large plasmids. A particularly useful method for this purpose is to partially digest the plasmid DNA under mild conditions for a short period of time employing a restriction endonuclease having a recognition sequence of at least four nucleotides. Desirably, the fragments obtained will be from about 10 to 20 kbp in length.

The conditions for the partial digest will generally include times of from about one to five minutes, temperatures of from about 10° to 30° C., more usually of from about 15° to 25° C. and ratios of about 10 to 50 μg plasmid DNA per unit of restriction enzyme. Of particular interest as the restriction enzyme is Sau3AI, although other restriction enzymes may be employed, such as BamHI, HindIII, etc. Other conditions, such as salt concentrations, buffer, and the like, will be those specified by the supplier.

The resulting mixture of linear and circular DNA is then isolated in accordance with conventional ways, e.g., extraction with phenol and chloroform followed by precipitation with ethanol.

The resulting DNA may be introduced into any convenient cloning vector, only the linear DNA being capable of ligation. Alternatively, linear DNA may be enriched by gel electrophoresis, gradient centrifugation, or the like, prior to insertion into a vector.

A large number of cloning vectors for fragments of 10 to 20 kbp are available and may be used. Illustrative cloning vectors include lambda, Charon 4A, pBR322, EMBO-4, or the like. Usually, for cloning, it is convenient to use a strain of *E. coli*, where the bacteria can be grown to high density and the vector allows for selection. Thus, the desired sequence can be obtained in relatively large amounts for subsequent manipulation. A wide variety of markers are known which provide prototrophy in an auxotrophic host, biocide resistance, e.g., antibiotics, toxins, heavy metals, etc., immunity, or the like.

The clones resulting from the transformants or transfectants may be screened for the expression of a polypeptide having immunogenic properties analogous to the naturally-occurring BTI endotoxin. Therefore, to simplify the screening method, one may prepare antibodies in accordance with conventional ways, either polyclonal or monoclonal, which specifically recognize the BTI endotoxin. The antibodies may be absorbed with proteins from the host to reduce the potential of cross-reactivity, which would result in false positive clones. Conveniently, the host or host proteins may be bound to a convenient support and the antiserum contacted with the antigens and unbound antiserum isolated.

The clones may then be screened with the antiserum, followed by labeling the bound antiserum with an appropriate label. Conveniently, the antibodies bound by the clones may be labeled with a radioisotope, enzyme, or fluorescer, as desired and is conventional in the field. The clone or the colonies of individual clones may be lysed and the plaque contacted with the antibody. By having the antigens present in the host fixed to a support, after washing away non-specifically-bound antibodies and label, the label at a particular site will indicate the presence of the endotoxin. Usually, the clones are grown on an agar nutrient medium and lysed (if required), followed by contacting the clones with an indexed filter, e.g., nitrocellulose filter, so as to transfer a portion of the clone-encoded proteins to the filter. In this way, the particular clones showing positive results may be located from the site on the filter.

Clones which have been detected to have a positive immune response to the BTI endotoxin antiserum may then be grown and the cells or lysates tested for insecticidal activity. The insecticidal activity can be demonstrated by combining the cells or lysates with larvae of an insect known to be sensitive to BTI endotoxin. An illustrative insect is *Aedes aegypti*.

Various organisms may be employed for expressing the polypeptide having biological activity analogous to BTI endotoxin. Illustrative hosts include *E. coli, B. megaterium, B. thermophilus, B. subtilis,* or the like; that is, bacteria which can provide for transcription and translation of the insecticidal polypeptide, particularly those bacteria which can recognize the transcriptional and translational regulatory signals recognized by *B. thuringiensis.*

If desired, the large fragment obtained by partial digestion may be further manipulated to provide for a smaller fragment, which may retain some or all of the regulatory signals associated with expression or some or all of the regulatory signals may be substituted or augmented. Manipulation may involve partial or complete digestion with one or more restriction enzymes, whereby the resulting fragments, generally ranging from about 500 to 5,000bp may be cloned and screened for the presence of the desired gene. Screening may include DNA probes, expression in expression vector systems, cells irradiated with ultra-violet radiation, in vitro translation, immunoprecipitations, screening for messenger RNA, or the like.

The expression product may be produced in a variety of forms, which may include soluble protein, which is secreted or retained by the organism or the protein may form inclusion bodies in the host organism. For secretion, various constructions may be employed, where the gene coding for the BTI endotoxin is inserted downstream and in reading frame with host secretory leader and processing signals; in this way, the resulting polypeptide may be secreted and processed and obtained in the nutrient medium. See, for example, Palva et al., *Gene* (1983) 22:229–235. Alternatively, the protein may be formed in the cytoplasm of the host and retained in the cytoplasm, where it may remain in soluble form or form inclusion bodies and the organism used or lysed and the protein isolated.

The host may be lysed by conventional ways, e.g., detergents, enzymatic degradation, or the like, and the protein isolated and purified by chromatography, electrophoresis, extraction, or the like. The protein may then be used as an insecticide. Alternatively, the organisms may be harvested and dried and used without further modification.

The BTI endotoxin may be formulated in a variety of ways, being incorporated with a variety of additives, depending upon its particular use. The endotoxin may be formulated with wetting agents, detergents, stabilizers, adhering agents, spreading agents, other insecticides, or the like. Usually, the endotoxin will be at least about 0.1% and not more than about 100% by weight of the formulation, more usually of from about 0.15 to 0.8 weight percent of the formulation, as described in Lacey et al., *Tropen Med. Parasit.* (1982) 33:97–101.

The following examples are offered by way of illustration and not by way of limitation.

EXPERIMENTAL

The gene for the BTI endotoxin was isolated from *B. thuringienis* var. *israelensis* strain ONR-60A, grown to late log phase. The plasmids were isolated and purified by alkaline lysis procedure, followed by successive precipitations with sodium acetate, isopropanol and ethanol (Birnboim and Doly, *Nucleic Acids Res.* (1979) 7.1513). The closed circular plasmids were freed from chromosomal DNA by banding to equilibrium through CsCl density gradients containing ethidium bromide. The plasmid DNA was partially digested with the restriction endonuclease Sau3AI, where the BTI plasmid DNA was incubated with Sau3AI for three minutes at 21° at a DNA to enzyme concentration of 20 $\mu$g plasmid DNA to one unit Sau3AI, with salt and buffer concentrations as specified by the supplier, Bethesda Research Laboratories. The conditions minimized cleavage of small plasmids, while providing linear fragments from the large plasmids of from about 10 to 20 kbp. Digestion was terminated by the addition of an equal volume of phenol saturated with the aqueous buffer.

The Sau3AI digest was freed of proteins by successive extractions with phenol and chloroform, followed by precipitation in two volumes of ethanol. The linear BTI DNA was then dissolved in Tris buffer (10 mM, pH 8.0) containing EDTA (1 mM), and ligated with T4 DNA ligase (New England Biolabs) to BamHI-cleaved DNA segments from the bacteriophage cloning vector $\lambda$L47.1 (Loenen and Brammar, *Gene* (1980) 10:249–259). The recombinant DNA was packaged in vitro into infectious phage particles that were then used to infect *E. coli* strain Q359, a P2 lysogen.

All the plaques resulting from this procedure represented clones with recombinant genomes (Loenen and Brammar, supra). These plaques were then screened for the expression of BTI antigens by an in situ radioimmunoassay (Walfield et al., *Science* (1982) 216:522–523). The immunological screening was performed with rabbit antiserum raised against purified BTI endotoxin. The endotoxin had been obtained from sporulating cultures of BTI that were harvested and washed in a salt solution. The endotoxin-containing crystals were prepared by centrifugation. BTI crystals were purified by sedimentation to equilibrium in sodium bromide density gradients. The antigen for injection into rabbits was equal parts crystals and alkali-solubilized crystals, which had been neutralized with acid. Rabbits were injected with antigen on days 1, 14 and 21 and the immune sera collected on day 28. The sera were specific for BTI and not *B. thuringiensis* var. kurstaki crystal preparations. Prior to use in screening plaques of the λL47.1 -BTI recombinants, a BTI rabbit antiserum was treated with an *E. coli* immunoabsorbent made by linking the antigens of an *E. coli* Q359 sonicated lysate to CNBr-activated Sepharose 4B beads (Pharmacia Fine Chemicals). This treatment removed most immunoglobulins which bound to *E. coli* antigens from the rabbit serum.

The antigenic selection procedure on recombinant plaques yielded eleven clones which were specifically reactive with BTI antisera. One of the clones selected for further testing was designated BTI A4-1. The assay employed was a modification of that described by Tyrell et al., *Appl. Environ. Microbiol.* (1979) 38:656-658. In this assay, a number of third instar larvae of *Aedes aegypti* are placed in separate containers in a small volume of water. The lysate is administered in the water and the mosquitoes are incubated at room temperature for three to six days, at which time mortality is observed. The *E. coli* lysates are prepared by infecting the host bacteria with the phage clones and growing overnight. The lysates are precipitated with acetone, followed by resuspension and dialysis in 20 mM Tris-HCl, pH 8. This procedure results in a two-fold concentration of a lysate. Larvae incubated in the lysates of BTI A4-1 displayed a markedly higher mortality after three to six days than did larvae incubated in lysates of the cloning vector λL47.1, as well as lysates of some of the other recombinant phage clones. The endotoxin is likely to be produced in a soluble, rather than crystalline form, as was observed with the kurstaki recombinant plasmids (Schnepf and Whitely, supra). The soluble form has been found to have a lower toxicity than the crystalline toxin (Thomas and Ellar, supra).

The presence of the BTI endotoxin was also shown by analysis of the proteins produced by the A4-1 lysate of *E. coli*. The polypeptides in an ammonium sulfate precipitated fraction from the clone were compared to polypeptides found in a lysate of λL47.1 and in BTI crystals. The lysate proteins and crystal proteins were analyzed by electrophoretic transfer to a nitrocellulose filter after sodium dodecyl sulfatepolyacrylamide gel electrophoresis. The nitrocellulose filter was then reacted with the immunoabsorbed BTI antiserum and probed with $^{125}$I-labeled *S. aureus* protein A (Walfield et al., supra).

An autoradiograph of the electrophoretic blot showed that the ammonium sulfate precipitant from BTI A4-1 lysate contained a polypeptide that was reactive with the BTI antiserum. The BTI A4-1-encoded polypeptide displayed a mobility in the polyacrylamide gel identical to the mobility of the predominant BTI antigen extracted from the authentic BTI crystals. No such BTI-specific reactant was observed in the λL47.1 lysate. Restriction endonuclease analysis on agarose gel of the DNA of BTI A4-1 showed that a segment of BTI DNA approximately 13 kbp long.

In accordance with the subject invention, novel proteins are produced providing for insecticidal activity against dipteran insects; the proteins are produced by expression of DNA sequences encoding for at least a portion of the BTI endotoxin, where the proteins are produced in other than the native host. By employing other than the native hosts, the insecticidal proteins can be produced economically and efficiently without requiring the complex nutritional requirements of the native host. Thus, a protein which is ecologically-acceptable can be employed for controlling a variety of insect pests.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising a DNA sequence in bacteriophage lambda SYN A 4-1 having A.T.C.C. Accession No. 40098 and encoding BTI endotoxin having a molecular weight of 58,000 daltons on polyacrylamide-SDS gels joined to a replicon other than the native BTI plasmid replicon associated as found in *B. thuringiensis*.

2. A DNA construct according to claim 1, wherein said DNA sequence is obtained from a plasmid from *B. thuringiensis* var. *israelensis* and said sequence is of less than about 15 kbp.

3. A DNA construct according to claim 2, wherein said replicon is functional in *E. coli*.

4. A DNA construct according to claim 1, wherein said construct comprises said DNA sequence inserted into a BamHI restriction site of bacteriophage cloning vector λ L47.1.

* * * * *